US006670353B2

(12) United States Patent
Reed et al.

(10) Patent No.: US 6,670,353 B2
(45) Date of Patent: Dec. 30, 2003

(54) OXIME-GROUP CONTAINING OESTRONE SULPHATASE INHIBITORS

(75) Inventors: Michael John Reed, London (GB); Barry Victor Lloyd Potter, Bath (GB)

(73) Assignee: Sterix Limited, Oxford (GB)

(*) Notice: Subject to any disclaimer, the term of this patent is extended or adjusted under 35 U.S.C. 154(b) by 0 days.

(21) Appl. No.: 09/572,237

(22) Filed: May 17, 2000

(65) Prior Publication Data

US 2002/0198396 A1 Dec. 26, 2002

Related U.S. Application Data

(63) Continuation-in-part of application No. PCT/GB98/03620, filed on Dec. 3, 1998.

(30) Foreign Application Priority Data

Dec. 4, 1997 (GB) ............................................... 9725749

(51) Int. Cl.$^7$ ............................ A61K 31/56; C07J 41/00
(52) U.S. Cl. ........................................ 514/182; 552/519
(58) Field of Search ......................... 558/48; 514/601, 514/445, 473, 182; 552/519

(56) References Cited

U.S. PATENT DOCUMENTS

| | | | | |
|---|---|---|---|---|
| 5,047,431 A | * | 9/1991 | Schickaneder et al. | 514/648 |
| 5,273,993 A | * | 12/1993 | Lo et al. | 514/400 |
| 5,556,847 A | * | 9/1996 | Johnson et al. | 514/178 |
| 5,567,831 A | * | 10/1996 | Li | 554/43 |
| 5,571,933 A | * | 11/1996 | Li et al. | 552/521 |
| 5,604,215 A | * | 2/1997 | Reed et al. | 514/178 |
| 5,616,574 A | * | 4/1997 | Reed et al. | 514/178 |
| 5,763,492 A | | 6/1998 | Johson et al. | 514/178 |
| 5,830,886 A | * | 11/1998 | Reed et al. | 514/178 |
| 5,861,390 A | * | 1/1999 | Reed et al. | 514/178 |
| 6,011,024 A | * | 1/2000 | Reed et al. | 514/171 |
| 6,017,904 A | * | 1/2000 | Reed et al. | 514/75 |
| 6,083,978 A | * | 7/2000 | Reed et al. | 514/457 |

FOREIGN PATENT DOCUMENTS

| | | | |
|---|---|---|---|
| GB | 1 398 026 | | 6/1975 |
| GB | 1398026 | * | 6/1975 |
| WO | WO 93/05064 | | 3/1993 |
| WO | WO 99/27936 | | 6/1999 |
| WO | WO 00/18397 | | 4/2000 |

OTHER PUBLICATIONS

Bioorganic & Medicinal Chemistry Letters, vol. 7, No. 24, pp. 3075–3080, 1997, Woo et al.
Journal of Steroid Biochemistry and Molecular Biology, vol. 55, No. 3/4, pp. 395–403, Dec. 1995., Eiger et al.

* cited by examiner

Primary Examiner—Barbara P. Badio
(74) Attorney, Agent, or Firm—Frommer Lawrence & Haug; Thomas J. Kowalski

(57) ABSTRACT

A sulphamate compound suitable for use as an inhibitor of oestrone sulphatase (E.C.3.1.6.2) is described. The compound is a polycyclic compound comprising at least two ring components, wherein the polycyclic compound comprises at least one sulphamate group attached to at least one of the ring components, and wherein at least one oxime group is attached to or is part of at least one of the ring components.

40 Claims, No Drawings

OXIME-GROUP CONTAINING OESTRONE SULPHATASE INHIBITORS

This application is a continuation-in-part of PCT/GB98/03620, filed Dec. 3, 1998 and designating the U.S., and published as WO 99/27936, on Jun. 10, 1999 and claiming priority from British application 9725749.7, filed Dec. 4, 1997; Reference is also made to U.S. Pat. Nos. 6,017,904, 6,011,024, 5,861,390, 5,830,886, 5,616,574, and 5,604,215 and allowed application Ser. No. 09/125,255, filed Aug. 14, 1998, and Ser. No. 09/142,194, filed Sep. 2, 1998. Each of the foregoing applications, patents and publications and all documents cited or referenced therein ("application cited documents") and all documents cited or referenced in this specification ("herein cited documents") and all documents referenced or cited in herein cited documents and in application cited documents, including during the prosecution of any of the application cited documents, are hereby incorporated herein by reference.

The present invention relates to a compound.

In particular the present invention relates to a compound and to a pharmaceutical composition comprising the compound. The present invention also relates to the use of that compound in the field of medicine.

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters. Examples of such inhibitors are sulphamate ester derivatives of steroids.

As is well known in the art, steroids have the general formula of:

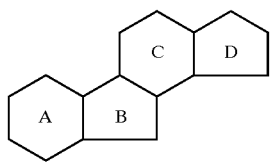

In the above formula, the ring components have been labelled in the conventional manner.

A preferred compound of PCT/GB92/101587 is oestrone-3-sulphamate (otherwise known as "EMATE"), which has the following structure:

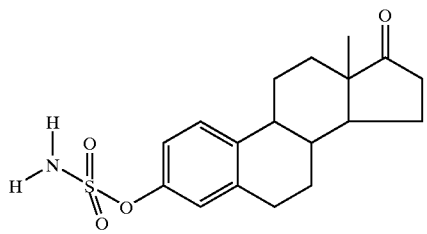

It is known that EMATE is a potent E1-STS inhibitor as it displays more than 99% inhibition of E1-STS activity in intact MCF-7 cells at 0.1 μM. EMATE also inhibits the E1-STS enzyme in a time- and concentration-dependent manner, indicating that it acts as an active site-directed inactivator.

Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol.

Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms—as in oestrone-3-N-sulphamate and oestrone-3-S-sulphamate—these analogues are weaker non-time-dependent inactivators.

Although optimal potency for inhibition of E1-STS may have been attained in EMATE, it is possible that oestrone may be released during sulphatase inhibition, and that EMATE and its oestradiol congener may possess oestrogenic activity.

The present invention seeks to provide novel compounds suitable for the inhibition of E1-STS but preferably wherein those compounds also have an oestrogenic effect.

Certain aspects of the present invention are presented in the accompanying claims.

A key advantage of the present invention is that the sulphamate compounds of the present invention can act as E1-STS inhibitors.

Another advantage of the compounds of the present invention is that they may be potent in vivo.

In addition, the compounds of the present invention can be used as oestrogenic compounds. Preferably some of the compounds are potent oestrogenic compounds. More preferably some of the compounds are highly oestrogenic compounds.

In a preferred embodiment therefore, the present invention therefore provides sulphamate compounds which are both steroid sulphatase inhibitors and oestrogenic.

The compounds of the present invention are also advantageous in that they may be orally active.

The sulphamate compounds of the present invention are believed to be useful for the treatment of breast cancer, or endocrine-dependent cancers, or endocrine- or oestrogen-dependent conditions and/or illnesses and/or cancers; see also documents cited herein (compounds therein also so useful).

In addition, the sulphamate compounds of the present invention are useful for the treatment of non-malignant conditions, such as the prevention of auto-immune diseases, particularly when pharmaceuticals may need to be administered from an early age.

The sulphamate compounds of the present invention are also believed to have therapeutic uses other than for the treatment of endocrine-dependent cancers, such as the treatment of autoimmune diseases and hormone replacement therapy.

The sulphamate compounds of the present invention are also believed to be useful for birth control etc.

These and further aspects of the present invention are now described.

Some or all of the ring components may be fused together or joined via one or more suitable spacer groups. The present invention also encompasses combinations thereof.

The term "sulphamate" as used herein includes an ester of sulphamic acid, or an ester of an N-substituted derivative of sulphamic acid, or a salt thereof.

Preferably, the sulphamate group has the formula:

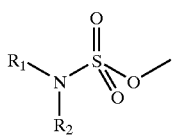

wherein each of $R_1$ and $R_2$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

In one preferred embodiment of the present invention, the hydrocarbyl group is a hydrocarbon group.

Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably, $R_1$ and $R_2$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl ($-PhCH_3$; o-, m- or p-). Where $R_1$ and $R_2$ represent cycloalyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

Within the values alkyl, cycloalkyl, alkenyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl.

In some preferred embodiments, at least one of $R_1$ and $R_2$ is H.

The polycyclic compound can comprise at least two ring components, or least three ring components, or least four ring components.

Preferably, the polycyclic compound comprises four ring components.

Preferably the polycyclic compound will contain, inclusive of all substituents, no more than 50 about carbon atoms, more usually no more than about 30 to 40 carbon atoms.

Preferred polycyclic compounds are those that are based on steroidal ring structures, that is to say a cyclopentanophenanthrene skeleton.

Thus, a preferred polyclic compound of the present invention has a structure similar to a steroidal structure but wherein an oxime group is attached to or is part of the D ring.

In this regard, the structure of the preferred polycyclic compound can be presented as:

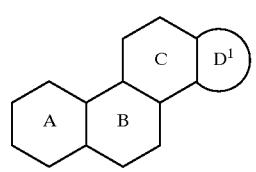

(I)

wherein ring $D^1$ represents the combination of a ring and the oxime group (i.e. the oxime group is part of or is attached to the ring component). The ring of $D^1$ may be substituted or unsubstituted, saturated or unsaturated. The rings A, B and C—which are similar to those of a steroidal nucleus—may be substituted or unsubstituted, saturated or unsaturated.

A preferred example of $D^1$ has the formula:

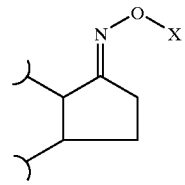

wherein the)— symbols represent the ring of $D^1$ being joined to the remainder of the steroidal structural formula;

and X represents H or a suitable substituent. An example of a suitable substituent is a hydrocarbyl group.

A further preferred example of $D^1$ has the formula:

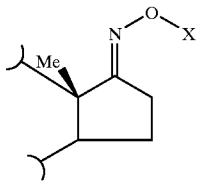

wherein the)— symbols represent the ring of $D^1$ being joined to the remainder of the steroidal structural formula; and X represents H or a suitable substituent. An example of a suitable substituent is a hydrocarbyl group. Here the indicated Me group is vertical.

As indicated, the ring of $D^1$ may be substituted with suitable groups—such as alkyl, hydroxy, halo etc. However, in a preferred embodiment, the ring atoms of $D^1$ that are not associated with neighbouring ring(s) are unsubstituted. By way of example these ring atoms are indicated below as 1 and 2 for the above presented preferred formula:

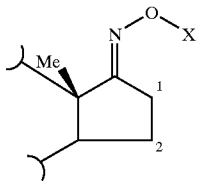

In compounds of the present invention the oxime group can be of either geometrical isomeric form. For example, the oxime group can be the syn isomer. In a preferred embodiment, the oxime group is the anti isomer. By way of example, the above presented formulae for $D^1$ show the anti isomeric structure.

Thus, the present invention encompasses compounds that have geometrical isomers. The compounds may be present in just one isomeric form or in combinations thereof. In one preferred embodiment, the compound is present as at least the anti isomer. In another preferred embodiment, the compound is present only as the anti isomer.

Examples of suitable preferred steroidal nuclei rings A–C for the rings A–C of the compounds of the present invention include rings A–C of oestrone and dehydroepiandrosterone.

Preferred steroidal nuclei having suitable rings A–C for the rings A–C of the compounds of the present invention are:

oestrones and substituted oestrones, viz:
  oestrones
  2-OH-oestrone
  2-methoxy-oestrone
  4-OH-oestrone
  6α-OH-oestrone
  7α-OH-oestrone
  16α-OH-oestrone
  16b-OH-oestrone
oestradiols and substituted oestradiols, viz:
  2-OH-17β-oestradiol
  2-methoxy-17β-oestradiol
  4-OH-17β-oestradiol
  6α-OH-17β-oestradiol
  7α-OH-17β-oestradiol
  16α-OH-17α-oestradiol
  16β-OH-17α-oestradiol
  16β-OH-17β-oestradiol
  17α-oestradiol
  17β-oestradiol
  17α-thinyl-17β-oestradiol
oestriols and substituted oestriols, viz:
  oestriol
  2-OH-oestriol
  2-methoxy-oestriol
  4-OH-oestriol
  6α-OH-oestriol
  7α-OH-oestriol
dehydroepiandrosterones and substituted dehydroepiandrosterones, viz:
  dehydroepiandrosterones
  6α-OH-dehydroepiandrosterone
  7α-OH-dehydroepiandrosterone
  16α-OH-dehydroepiandrosterone
  16β-OH-dehydroepiandrosterone In general terms the ring system $ABCD^1$ may contain a variety of non-interfering substituents. In particular, the ring system $ABCD^1$ may contain one or more of hydroxy, alkyl especially lower $(C_1-C_6)$ alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower $(C_1-C_6)$ alkoxy, e.g. methoxy, ethoxy, propoxy etc., alkinyl, e.g. ethinyl, or halogen, e.g. fluoro substituents.

In an alternative embodiment, the polyclic compound may not contain or be based on a steroid nucleus. In this regard, the polyclic compound may contain or be based on a non-steroidal ring system—such as diethylstilboestrol, stilboestrol and other ring systems.

In formula (I), the at least one sulphamate group is attached to any one or more of the ring components.

Preferably, the polycyclic compound has a steroidal structure and wherein the sulphamate group is attached to the A ring.

Preferably, the sulphamate group is attached to the 3 position of the A ring.

A preferred compound has the formula:

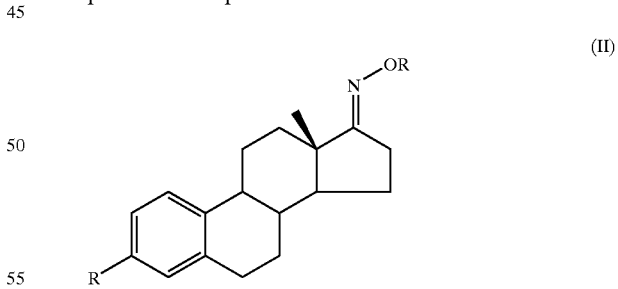

(II)

wherein R denotes a sulphamate group as described above. Here the indicated Me group is vertical.

Preferably, R is the above-mentioned preferred formula for the sulphamate group. In this regard, it is preferred that at least one of $R_1$ and $R_2$ is H.

In formula (II), the oxime group can be of either geometrical isomer form. For example, the oxime group can be the syn isomer. In a preferred embodiment, the oxime group is the anti isomer.

A more preferred compound has the formula:

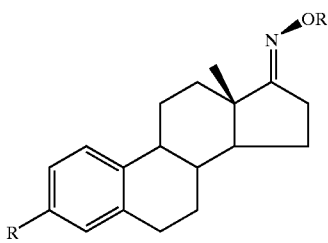

(III)

wherein R denotes a sulphamate group as described above.

Preferably, R is the above-mentioned preferred formula for the sulphamate group. In this regard, it is preferred that at least one of $R_1$ and $R_2$ is H.

In formula (III), the oxime group can be of either geometrical isomer form. For example, the oxime group can be the syn isomer. In a preferred embodiment, the oxime group is the anti isomer.

Preferably, if the sulphamate group of the compound of the present invention were to be replaced with a sulphate group to form a sulphate compound then that sulphate compound would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 mmoles when incubated with steroid sulphatase EC 3.1.6.2 at pH 7.4 and 37° C.

In another preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 µmoles when incubated with steroid sulphatase EC 3.1.6.2 at pH 7.4 and 37° C.

In a highly preferred embodiment, the compound of the present invention is not hydrolysable by an enzyme having steroid sulphatase (E.C. 3.1.6.2) activity.

The sulphamate compounds of the present invention may be prepared by reacting an appropriate alcohol with the appropriate sulfamoyl chloride, $R_1R_2NSO_2Cl$.

Preferred conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, adjuvants, excipients, diluents etc. and usually for parenteral administration. Approximate effective dose rates are in the range 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4hydroxyandrostenedione (4-OHA).

In the method of treatment, the subject is preferably a mammal, more preferably a human. For some applications, preferably the human is a woman.

In summation, the present invention provides novel compounds for use as steroid sulphatase inhibitors, and pharmaceutical compositions containing them. The compounds also have a oestrogenic activity—particularly when compared with EMATE. Thus, the present invention provides novel compounds having steroid sulphatase inhibitory activity which, in some cases, have extremely high activity levels.

In addition, the present invention provides novel compounds having oestrogenic activity which, in some cases, have extremely high activity levels.

It will be appreciated that the present invention also includes the following:

(i) a compound of the present invention or a pharmaceutically acceptable salt of the compound, or a pharmaceutically acceptable solvate of the compound or the salt;

(ii) one or more processes for the preparation of a compound of the present invention or a pharmaceutically acceptable salt of the compound, or a pharmaceutically acceptable solvate of the compound or the salt;

(iii) novel intermediates for use in those processes;

(iv) a pharmaceutical composition comprising a compound of the present invention, or a pharmaceutically acceptable salt of the compound, or a pharmaceutically acceptable solvate of the compound or the salt, admixed with a pharmaceutically acceptable diluent, carrier or excipient;

(v) a compound of the present invention, or a pharmaceutically acceptable salt of the compound, or a pharmaceutically acceptable solvate of the compound or the salt or composition thereof, for use as a medicament;

(vi) the use of a compound of the present invention, or a pharmaceutically acceptable salt of the compound, or a pharmaceutically acceptable solvate of the compound or the salt or composition thereof, for the manufacture of a medicament for the inhibition of oestrone sulphatase;

(vii) the use of a compound of the present invention, or a pharmaceutically acceptable salt of the compound, or a pharmaceutically acceptable solvate of the compound or the salt or composition thereof, for the manufacture of a medicament for the inhibition of oestrone sulphatase;

(viii) a method for the inhibition of oestrone sulphatase which method comprises administering to a subject an effective amount of a compound of the present invention or a pharmaceutically acceptable salt of the compound, or a pharmaceutically acceptable solvate of the compound or the salt or composition thereof;

(ix) a method for inhibition of oestrone sulphatase which method comprises administering to a subject an effective amount of a compound of the present invention or a pharmaceutically acceptable salt of the compound, or a pharmaceutically acceptable solvate of the compound or the salt or composition thereof.

In the above-mentioned uses and methods, the subject is typically a mammal.

The pharmaceutically acceptable salts of the compounds of/for use in the present invention include suitable acid addition or base salts thereof. For a review on suitable pharmaceutical salts see Berge et al, J Pharm Sci, 66, 1–19 (1977).

By way of example, suitable acid addition salts are formed from acids which form non-toxic salts. Suitable examples of such salts are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and p-toluenesulphonate salts.

Also by way of example, suitable base salts are formed from bases which form non-toxic salts. Suitable examples thereof are the aluminium, calcium, lithium, magnesium, potassium, sodium, zinc, N-benzyl-N-(2-phenylethyl) amine, 1-adamantylamine and diethanolamine salts.

As mentioned above, the present invention also covers pharmaceutical compositions comprising the compounds of the present invention. In this regard, and in particular for human therapy, even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice.

By way of example, in the pharmaceutical compositions of the present invention, the compounds of the present invention may be admixed with any suitable binder(s), lubricant(s), suspending agent(s), coating agent(s), solubilising agent(s).

Tablets or capsules of the compounds may be administered singly or two or more at a time, as appropriate. It is also possible to administer the compounds in sustained release formulations.

Typically, a physician will determine the dosage which will be most suitable for an individual patient and it will vary with the age, weight and response of the particular patient.

Alternatively, the compounds of/for use in the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, such as at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

Thus the invention provides a pharmaceutical composition comprising a compound of the present invention, or a pharmaceutically acceptable salt thereof, or a pharmaceutically acceptable solvate of either entity, together with a pharmaceutically acceptable diluent, excipient or carrier.

The invention further provides a compound of the present invention, or a pharmaceutically acceptable salt thereof, or a pharmaceutically acceptable solvate of either entity, or a pharmaceutical composition containing any of the foregoing, for use as a human medicament.

The present invention also provides a veterinary formulation comprising a compound of the present invention, or a veterinarily acceptable salt thereof, or a veterinarily acceptable solvate of either entity, together with a veterinarily acceptable diluent, excipient or carrier.

For veterinary use, a compound of the present invention or a veterinarily acceptable salt thereof, or a veterinarily acceptable solvate of either entity, is typically administered as a suitably acceptable formulation in accordance with normal veterinary practice and the veterinary surgeon will determine the dosing regimen and route of administration which will be most appropriate for a particular animal. However, as with human treatment, it may be possible to administer the compound alone for veterinary treatments.

In addition, the present invention provides a compound of the present invention, or a veterinarily acceptable salt thereof or a veterinarily acceptable solvate of either entity, or a veterinary formulation containing any of the foregoing, for use as an animal medicament. Reference is also made to WO 99/27935, and concurrently-filed U.S. application Ser. No. 09/572,246.

The present invention will now be described only by way of example.

In the examples reference is made to steroid sulphatase inhibition. This is determined according to the teachings of PCT/GB92/01587 wherein the ability of compounds to inhibit oestrone sulphatase activity is assessed using either intact MCF-7 breast cancer cells or placental microsomes. For ease of reference, those teachings are repeated here as Example 1.

EXAMPLE 1

Inhibition of Steroid Sulphatase Activity in MCF-7 Cells by Oestrone-3-sulphamate Steroid sulphatase (Steroid sulphatase is defined as: Steryl Sulphatase EC 3.1.6.2.) activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm$^2$ tissue culture flasks were seeded with approximately 1×10$^5$ cells/flask using the above medium. Cells were grown to 80% confluency and medium was changed every third day.

Intact monolayers of MCF-7 cells in triplicate 25 cm$^2$ tissue culture flasks were washed with Earle's Balanced Salt Solution (EBSS from ICN Flow, High Wycombe, U.K.) and incubated for 3–4 hours at 37° C. with 5 pmol (7×10$^5$ dpm) [6,7-$^3$H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask was cooled and the medium (1 ml) was pipetted into separate tubes containing [$^{14}$C] oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C] oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each batch of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to assess cell membrane status and viability using the Trypan Blue exclusion method (Phillips, H. J. (1973) In: *Tissue culture and applications*, [eds: Kruse, D. F. & Patterson, M. K.]; pp. 406–408; Academic Press, New York).

Results for steroid sulphatase activity are expressed as the mean ±1 S.D. of the total product (oestrone+oestradiol) formed during the incubation period (20 hours) calculated for 10$^6$ cells and, for values showing statistical significance, as a percentage reduction (inhibition) over incubations containing no oestrone-3-sulphamate. Unpaired Student's t-test was used to test the statistical significance of results.

Inhibition of Steroid Sulphatase Activity in Placental Microsomes by Oestrone-3-sulphamate Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at −20° C. The protein concentration of the supernatants was determined by the method of Bradford (*Anal. Biochem.*, 72, 248–254 (1976)).

Incubations (1 ml) were carried out using a protein concentration of 100 mg/ml, substrate concentration of 20 mM [6,7-$^3$H]oestrone-3-sulphate (specific activity 60 Ci/mmol from New England Nuclear, Boston, Mass., U.S.A.) and an incubation time of 20 minutes at 37° C. Eight concentrations of the compounds to be tested may be employed: 0 (i.e. control); 0.05 mM; 0.1 mM; 0.2 mM; 0.4 mM; 0.6 mM; 0.8 mM; 1.0 mM. After incubation each sample was cooled and the medium (1 ml) was pipetted into separate tubes containing [$^{14}$C]oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C]oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C] oestrone added) and the specific activity of the substrate.

EXAMPLE 2

Oestrone Oxime

We prepared oestrone oxime according to the method described[3], but we used hydroxylamine hydrochloride instead of hydroxylamine acetate and obtained oestrone oxime in excellent yield, better than previously reported.

Of two possible geometrical isomers for 17-oximes, Wataru et al.[4] assumed they had the anti-form, because it is believed that this form of oximes[5] is more stable than the syn-form and that the transition state leading to the anti-oxime may have an energy lower than that in the case of the syn-isomer. Thus, the structure of the oestrone oxime isomer obtained was just assumed, and not confirmed by any special method such as NOE or X-ray crystallography. To prove and confirm which isomer was obtained from the reaction, we ran NOE experiment which did not work; perhaps because the hydroxyl group of the oxime is exchangeable. We proved the structure of oestrone oxime by X-ray crystallography and it was found indeed that only one geometrical isomer (anti-oxime isomer) was obtained.

Our study is the first to provide modern spectroscopic date and an X-ray crystal structure for oestrone oxime.

CHN analysis for oestrone oxime was alright, but by considering a small methanol content (from the crystallization solvent), which involved in hydrogen bonding to the molecule as X-ray shows, then the HN values are very close.

In the preparation of the oestrone oxime sulphamate, another compound is formed which could not be isolated because it is very polar. This compound could be the bis-sulphamate of the oxime.

Oestrone Oxime (1)

To a solution of oestrone (10 g, 36.982 mmol) in ethanol (300 ml), hydroxylamine hydrochloride (7.71 g, 111 mmol, 3 eq.), sodium hydroxide (3.0 g, 75 mmol, 2 eq.) and water (10 ml) were added. The mixture was refluxed for two hours. The cold mixture was poured into 1N HCl. The precipitate was filtered, washed with cold water and dried to give a white solid (10.132 g, 96%). For analysis, a sample was recrystallized from aqueous methanol to give 1 as colorless crystals. Mp.=249–251° C. (lit. Mp.=248–250° C.), IR (KBr) 1690 (—C=N—) cm$^{-1}$. $\delta_H$ (DMSO-d$_6$, 400 MHz) 0.85 (3H, s, C-18–CH$_3$),1.26–3.18 (15H, m), 6.44 (1.H, d, $J_{C\text{-}4\text{-}H \text{ and } C\text{-}2\text{-}H}$=2.13 Hz, C-4-H), 6.5 (1H, dd, $J_{C\text{-}2\text{-}H \text{ and } C\text{-}1\text{-}H}$=8.24 Hz and $J_{C\text{-}2\text{-}H \text{ and } C\text{-}4\text{-}H}$=2.44 Hz, C-2-H), 7.04 (1H, d, $J_{C\text{-}1\text{-}H \text{ and } C\text{-}2\text{-}H}$=8.55 Hz, C-1-H), 9.03 (1H, br s, C-3-OH) and 10.1 (1H, br s, C=N—OH). C$^{13}$ 167.99 (—C=N—), 155.025 (C-3), 137.103 (C-5 or C-10), 130.19 (C10 or C-5), 126.0 (C-1), 114.99 (C-4), 112.79 (C-2), 52.52 (C-8 or C-9 or C-14), 48.66 (CH$_3$ from methanol), 43.62 (C-8 or C-9 or C-14), 43.61 (C-13), 37.91 (C-8 or C-9 or C-14), 34.33, 29.13, 26.90, 25.99, 24.94 and 22.57 (C-6, C-7, C-11, C-12, C-15 and C-16) and 17.35 (C-18). MS: m/z (+ve ion FAB in m-NBA, rel. intensity) 439.3 [15, (M+H+NBA)$^+$], 286.3 [100, M+H)$^+$], 268.3 [20, (M-H$_2$O)], 243.3 (10), 178.2 (10), 159.1 (10), 133.1 (15), 102.0 (10) and 74.9 (10). MS: m/z (-ve ion FAB in m-NBA, rel. intensity) 437.3 [65, (M-H+NBA)$^+$], 284.2 [100, (M-H)$^-$], 258.1 (25), 229.1 (20), 215.1 (25), 195.1 (45), 178.1 (30), 139.1 (35), 108.0 (30) and 65.0 (10). Acc. MS: m/z (FAB)$^+$=286.18046 C$_{18}$H$_{24}$NO$_2$ requires 286.18072. Found C, 73.5; H, 8.27; N, 4.48; C$_{18}$H$_{23}$NO$_2$ requires C, 75.76; H, 8.12; N, 4.91.

Oestrone Oxime-3-O-sulphamate (2)

Oestrone oxime (1 g, 3.504 mmol) gave a crude product (1.33 g) which was fractionated on silica (200 g) with a chloroform/acetone gradient, and upon evaporation the second fraction gave a white residue (312 mg), which was recrystallized from acetone/hexane (1:2) to give 2 as white crystals (289.5 mg, 25%) mp.=174–176° C. IR (KBr) 3400–3280 (NH$_2$), 1710(—C=N—), 1390 (—SO$_2$—) cm$^{-1}$. $\delta_H$ (DMSO-d$_6$, 400 Mhz) 0.87 (3H, s, C-18–CH$_3$), 1.29–2.85 (15H, m), 6.98 (1H, d, $J_{C\text{-}4\text{-}H \text{ and } C\text{-}2\text{-}H}$=2.14 Hz, C-4-H), 7.02 (1H, dd, $J_{C\text{-}2\text{-}H \text{ and } C\text{-}1\text{-}H}$=8.55 Hz and $J_{C\text{-}2\text{-}H \text{ and } C\text{-}4\text{-}H}$=2.44 Hz, C-2-H), 7.35 (1H, d, $J_{C\text{-}1\text{-}H \text{ and } C\text{-}2\text{-}H}$=8.54 Hz, C-1-H), 7.9 (2H, s, exchanged with D$_2$O, C-3-SO$_2$NH$_2$) and 10.12 (1H, br s, C=N—OH). C$^{13}$ 167.71 (—C=N—), 147.86 (C-3), 138.1 and 137.86 (C-5 and C-10), 126.41 (C-1), 121.76 (C-4), 119.18 (C-2), 52.32 (C-8 or C-9 or C-14), 43.62 (C-8 or C-9 or C-14), 43.2 (C-13), 37.25 (C-8 or C9 or C-14), 34.12, 28.84, 26.35, 25.60, 24.78 and 22.4 (C-6, C-7, C-11, C-12, C-15 and C-16) and 17.17 (C-18). MS: m/z (+ve ion FAB in m-NBA, rel. intensity) 518.2 [90, (M+H+NBA)$^+$], 365.2 [100, (M+H)$^+$], 330.2 (10), 285.2 [10, (M-SO$_2$NH$_2$)$^+$]. MS: m/z (-ve ion FAB in m-NBA, rel. intensity) 517.2 [40, (M-H+NBA)$^+$], 363.2 [100, (M-H$^-$), 333.1 (10). Acc. MS: m/z (FAB)$^+$=365.15451 C$_{18}$H$_{25}$N$_2$O$_4$S requires 365.1535. Found C, 59.2; H, 6.84; N, 7.03; C$_{18}$H$_{23}$N$_2$O$_2$S requires C, 59.32; H, 6.64; N, 7.69.

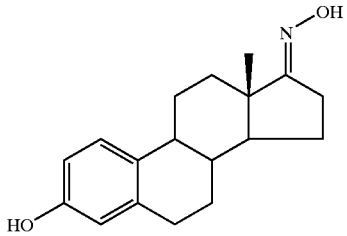

[1]

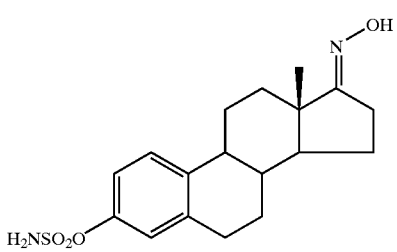

[2]

REFERENCES

1) Ivanenko T I, Kolomin L V, Golubovskaya L E and Pivnitskii K K. Synthesis and properties of 17-N-Substituted derivatives of 1,3,5 (10)-estratrienes. *Pharm. Chem. J.* 1982, 16, 751–56.
2) Peters R H, Crowe D F, Mitchell A A, Chong W K M and Tanabe M. 17-Desoxy estrogen analogues. *J. Med. Chem.* 1989, 32, 1642–52.
3) Bernard M R and Hayes F N. 17- and 17a-D-homosteroids. *Journal of American Chemical Society* 1955, 78, 639–643.
4) Nagata W, Sugasawa T, Narisada M, Okada T, Sasakura K, Murakami M and Hayase Y. Steroids and their O-alkyl derivatives. *Chem. Pharm. Bull.* 1966, 14, 174–186.
5) Kaufmann C S. Beckmann rearrangement of 17-keto steroids oximes. *J. Am. Chem. Soc.* 1951, 73, 1779.

EXAMPLE 3

Estrone-3-O-sulphamate-17-oxime

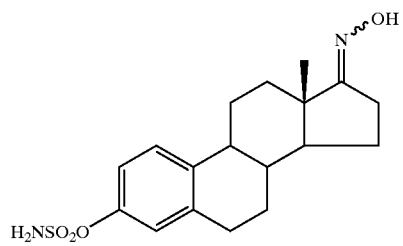

| INHIBITOR CONCENTRATION | % INHIBITION ($\bar{x} \pm$ S.D., n = 3) | |
| --- | --- | --- |
| | MCF-7 cells | PLACENTAL MICROSOMES |
| 10 $\mu$M | 99 ± 0.2 | 98.7 ± 0.1 |
| 1 $\mu$M | 98 ± 0.6 | 89.8 ± 0.2 |
| 0.1 $\mu$M | 96 ± 1.8 | 52.3 ± 0.1 |

-continued

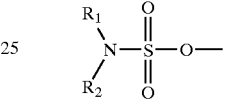

| | % INHIBITION ($\bar{x}$ ± S.D., n = 3) | |
|---|---|---|
| INHIBITOR CONCENTRATION | MCF-7 cells | PLACENTAL MICROSOMES |
| 10 nM | — | 19.3 ± 2.4 |
| 1 nM | — | 8.0 ± 3.3 |
| 0.1 nM | — | 2.9 ± 1.1 |

In Vivo Inhibition (Rat Liver Sulphatase)

99.2±0.42%. @ 2 mg/kg/dx5 ol, ORAL DOSE.

Examples 2 and 3 are further referenced in Annex 1.

EXAMPLE 4

Measurement of Estrogenic Activity

Compounds according to the present invention such as Compound 2 (such as at levels of 0.1 mg/Kg/day for five days) are administered orally to rats with another group of animals receiving vehicle only (propylene glycol). At the end of the study uteri are obtained and weighed with the results being expressed as uterine weight/whole body weight×100.

The results show that administration of Compound 2 has an effect on uterine growth, showing that the compound is oestrogenic.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

What is claimed is:

1. A sulphamate compound having the Formula (A):

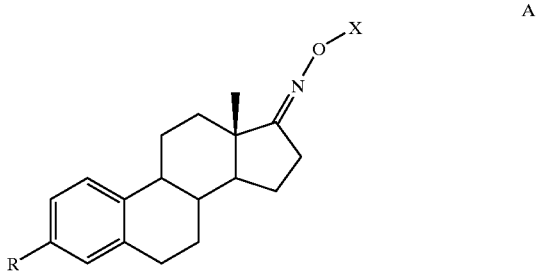

wherein R is a sulphamate group; X is selected from the group consisting of hydrogen, a hydrocarbyl group or R; and wherein the sulphamate compound is oestrogenic and exhibits an oestrogenic effect, and the sulphamate compound is an inhibitor of oestrone sulphatase.

2. The sulphamate compound according to claim 1, wherein the sulphamate group, R, has the formula $$\begin{array}{c} R_1 \\ \diagdown \\ N-S-O- \\ \diagup \\ R_2 \end{array} \begin{array}{c} O \\ \| \\ \| \\ O \end{array}$$

and wherein each of $R_1$ and $R_2$ is independently selected from H or a hydrocarbyl group.

3. The sulphamate compound according to claim 2, wherein at least one of $R_1$ and $R_2$ is H.

4. The sulphamate compound according to claim 3, wherein each of $R_1$ and $R_2$ is H.

5. The sulphamate compound according to claim 2, wherein each of $R_1$ and $R_2$ is independently selected from H, alkyl, cycloakyl, alkenyl and aryl, or together represent alkylene optionally containing one or more hetero atoms or groups in the alkylene chain.

6. The sulphamate compound to any one of claims 1, 2, 3, 4, or 5, wherein the oxime group is an anti isomer.

7. A sulphamate compound according to any one of claims 1, 2, 3, 4, or 5 wherein the compound is not hydrolysable by an enzyme having steroid sulphatase activity.

8. The compound of any one of claims 1, 2, 3, 4 or 5 wherein X is hydrogen.

9. The compound of any one of claims 1, 2, 3, 4 or 5 wherein X is a hydrocarbyl group.

10. The compound of claim 7 wherein X is hydrogen.

11. The compound of claim 7 wherein X is hydrocarbyl.

12. The compound of any one of claims 1, 2, 3, 4 or 5 wherein the estrogenic effect of the compound is greater than that of oestrone-3-sulphamate.

13. The compound of claim 8 wherein the estrogenic effect of the compound is greater than that of oestrone-3-sulphamate.

14. The compound of claim 9 wherein the estrogenic effect of the compound is greater than that of oestrone-3-sulphamate.

15. The compound of claim 10 wherein the estrogenic effect of the compound is greater than that of oestrone-3-sulphamate.

16. The compound of claim 11 wherein the estrogenic effect of the compound is greater than that of oestrone-3-sulphamate.

17. The compound of claim 1 wherein the estrogenic effect of the compound is greater than that of oestrone-3- sulphamate and the compound has the formula

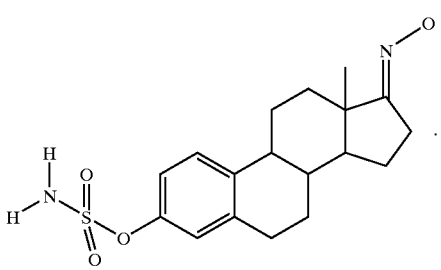

I

18. A pharmaceutical composition for inhibiting oestrone sulphatase in a subject in need thereof comprising the sulphamate compound of any one of claims 1, 2, 3, 4, or 5, and a pharmaceutically acceptable carrier, adjuvant, excipient or diluent.

19. The composition of claim 18 wherein X is hydrogen.

20. The composition of claim 18 wherein X is hydrocarbyl.

21. The composition of claim 19 wherein the estrogenic effect of the compound is greater than that of oestrone-3-sulphamate.

22. The composition of claim 20 wherein the estrogenic effect of the compound is greater than that of oestrone-3-sulphamate.

23. A method for inhibiting oestrone sulphatase in a subject in need thereof comprising administering to said subject the sulphamate compound according to any one of claims 1, 2, 3, 4, or 5.

24. A method for inhibiting steroid sulphatase and providing an estrogenic effect in a subject in need thereof comprising administering a steroid sulphatase inhibiting amount and an estrogenic effective amount of a compound of formula I

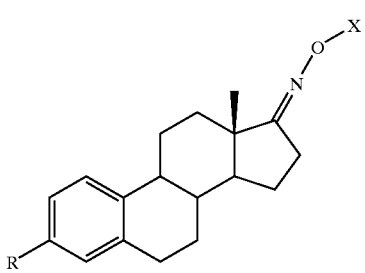

A wherein R is a sulphamate group; X is selected from the group consisting of hydrogen, a hydrocarbyl group or R.

25. The method of claim 24 wherein R has the formula

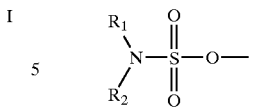

wherein each of $R_1$ and $R_2$ is independently selected from H or a hydrocarbyl group.

26. The method of claim 25 wherein at least one of $R_1$ and $R_2$ is H.

27. The method of claim 26 wherein $R_1$ and $R_2$ are H.

28. The method of claim 25 wherein $R_1$ and $R_2$ are independently selected from H, alkyl, cycloakyl, alkenyl and aryl, or together represent alkylene optionally containing one or more hetero atoms or groups in the alkylene chain.

29. The method of claim 24 wherein the oxime group is an anti isomer.

30. The method of claim 24 wherein the compound is not hydrolysable by an enzyme having steroid sulphatase activity.

31. The method of any one of claims 24–30 wherein X is hydrogen.

32. The method of any one of claims 24–30 wherein X is a hydrocarbyl group.

33. The method of any one of claims 24–30 wherein the estrogenic effect of the compound is greater than that of oestrone-3-sulphamate.

34. The method of claim 31 wherein the estrogenic effect of the compound is greater than that of oestrone-3-sulphamate.

35. The method of claim 32 wherein the estrogenic effect of the compound is greater than that of oestrone-3-sulphamate.

36. The method of claim 24 wherein the estrogenic effect of the compound is greater than that of oestrone-3-sulphamate and the compound has the formula

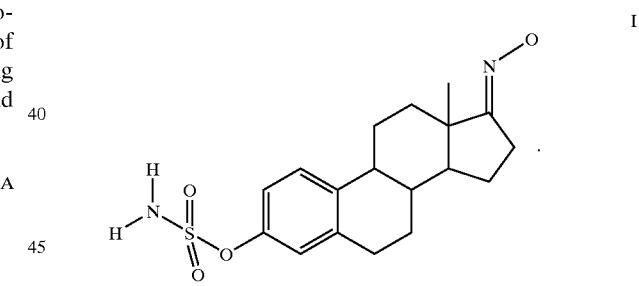

I

37. The method of claim 23 wherein X is hydrogen.

38. The method of claim 23 wherein X is hydrocarbyl.

39. The method of claim 37 wherein the estrogenic effect of the compound is greater than that of oestrone-3-sulphamate.

40. The method of claim 38 wherein the estrogenic effect of the compound is greater than that of oestrone-3-sulphamate.

* * * * *

UNITED STATES PATENT AND TRADEMARK OFFICE
CERTIFICATE OF CORRECTION

PATENT NO.       : 6,670,353 B2
APPLICATION NO.  : 09/572237
DATED            : December 30, 2003
INVENTOR(S)      : Reed et al.

It is certified that error appears in the above-identified patent and that said Letters Patent is hereby corrected as shown below:

In column 17 lines 2-14, delete the formula and insert therefor:

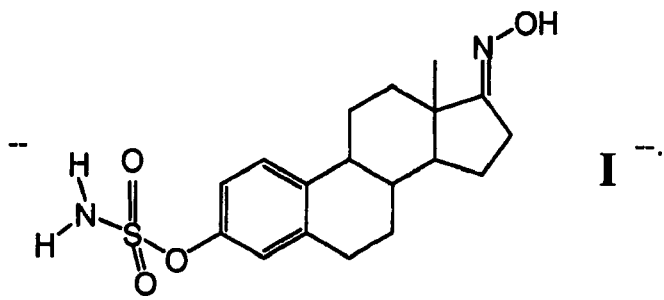

In column 18 lines 35-48, delete the formula and insert therefor:

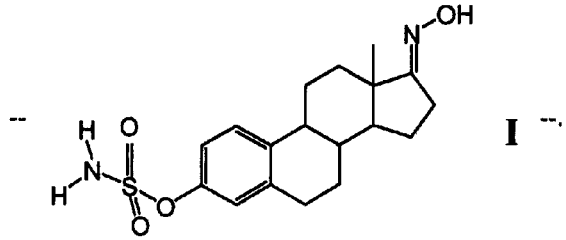

Signed and Sealed this

Twenty-ninth Day of January, 2008

JON W. DUDAS
*Director of the United States Patent and Trademark Office*